(12) United States Patent
Kleiner et al.

(10) Patent No.: US 8,715,569 B2
(45) Date of Patent: May 6, 2014

(54) POST ELECTRON BEAM STABILIZATION OF POLYMERIC MEDICAL DEVICES

(75) Inventors: Lothar W. Kleiner, Los Altos, CA (US); Fuh-Wei Tang, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 607 days.

(21) Appl. No.: 12/860,681

(22) Filed: Aug. 20, 2010

(65) Prior Publication Data

US 2012/0045362 A1 Feb. 23, 2012

(51) Int. Cl.
*A61L 2/00* (2006.01)
*B01J 19/08* (2006.01)
*A61F 2/00* (2006.01)
*G01N 23/00* (2006.01)

(52) U.S. Cl.
USPC ............ 422/22; 422/1; 422/186; 250/455.11; 250/492.3; 607/100

(58) Field of Classification Search
USPC .................... 422/1, 22, 186; 607/100, 154
See application file for complete search history.

(56) References Cited

U.S. PATENT DOCUMENTS

| | | | |
|---|---|---|---|
| 5,650,485 A * | 7/1997 | Sun et al. ................ | 528/483 |
| 2007/0065334 A1 | 3/2007 | Shalaby | |
| 2008/0169582 A1 | 7/2008 | Dave et al. | |
| 2011/0001271 A1 | 1/2011 | Hossainy et al. | |

FOREIGN PATENT DOCUMENTS

| | | |
|---|---|---|
| EP | 0 218 003 | 4/1987 |
| EP | 1 872 808 | 1/2008 |
| JP | 11 133196 | 5/1999 |
| JP | 2000 334028 | 12/2000 |
| WO | WO 03/037390 | 5/2003 |
| WO | WO 2006/034157 | 3/2006 |
| WO | WO 2007/142736 | 12/2007 |
| WO | WO 2010/017090 | 2/2010 |
| WO | WO 2010/019448 | 2/2010 |

OTHER PUBLICATIONS

Milicevic et al., "Thermal and crystallization behaviour of gamma irradiated PLLA", Radiation Physics and Chemistry 76, pp. 1376-1380 (Feb. 2007).*
International Search Report for PCT/US2011/057932 mailed Apr. 5, 2012, 11 pgs.
International Search Report for PCT/US2011/047974 mailed May 3, 2012, 10 pgs.
Milicevic et al., "Thermal and crystallization behaviour of gamma irradiated PLLA", Radiation Physics and Chemistry 76, pp. 1376-1380 (2007).

* cited by examiner

*Primary Examiner* — Monzer R Chorbaji
(74) *Attorney, Agent, or Firm* — Squire Sanders (US) LLP

(57) ABSTRACT

Methods are disclosed for chemically stabilizing a polymer stent after sterilization. The stent is exposed to a temperature above ambient for a period of time after radiation sterilization. The exposure reduces the concentration of free radicals generated by the radiation.

6 Claims, 4 Drawing Sheets

POST ELECTRON BEAM STABILIZATION OF POLYMERIC MEDICAL DEVICES

BACKGROUND OF THE INVENTION

1. Field of the Invention

This invention relates to methods of making stents from bioabsorbable polymers.

2. Description of the State of the Art

This invention relates to radially expandable endoprosthesis that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site. Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. A medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be bioresorbable. In many treatment applications, the presence of a stent in a body may be necessary for a limited period of time until its intended function is accomplished, for example, maintaining vascular patency to allow for remodeling of the vessel walls at an increased diameter. Therefore, stents fabricated from bioresorbable, bioabsorbable, and/or bioerodable materials, such as polymers, should be configured to completely resorb only after the clinical need for them has ended.

However, one of the challenges of making medical devices out of polymers is that properties of a polymer can deteriorate both during processing and after processing. These properties include mechanical properties such as strength and toughness and bioresorption kinetics. The processing steps in a fabrication process of a stent may be designed to maintain or instill in the stent particular ranges of the above properties that are crucial for treatment with the stent. Medical devices such as stents are typically stored for an indefinite period of time after fabrication is completed during which properties of the polymer can change as a function of time away from such desirable or crucial ranges. Therefore, methods are needed that reduce or eliminate undesirable changes in properties.

SUMMARY OF THE INVENTION

Various embodiments of the present invention include a method of stabilizing a stent comprising: sterilizing a stent made of polymer with radiation exposure, wherein the radiation exposure generates free radicals within the polymer; exposing the stent to a temperature above ambient to increase a temperature of the stent, wherein the increase in temperature reduces the concentration of free radicals and increases the decay kinetics of free radicals leading to their disappearance and thereby reducing the chemical degradation of the polymer due to the sterilization.

Further embodiments of the present invention include a method of stabilizing a stent comprising: sterilizing a stent made of polymer with radiation, wherein the radiation exposure generates free radicals within the polymer; exposing the stent to a temperature cycle including increasing the exposure temperature to a specified temperature above ambient, decreasing the exposure temperature to a minimum temperature; repeating the temperature cycle one or more times, wherein the repeated cycles reduce the concentration of free radicals thereby reducing the chemical degradation of the polymer due to the sterilization.

DETAILED DESCRIPTION OF THE INVENTION

Figure 1:
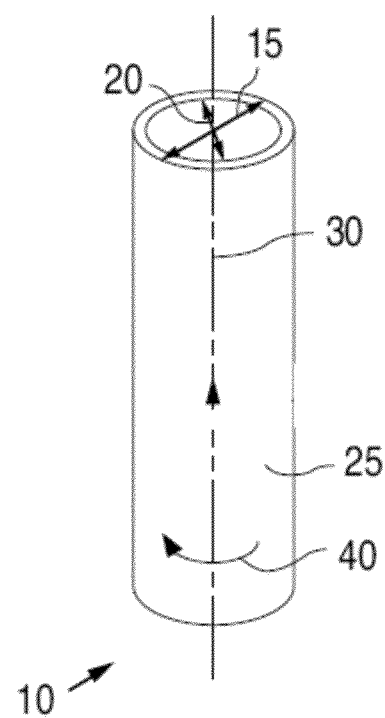
FIG. 1 depicts a tube from which a stent is manufactured.

Embodiments of the present invention relate to stabilizing polymeric implantable medical devices such as stents, after electron beam (e-beam) sterilization. More generally, embodiments of the present invention may also be used on devices, including, but not limited to, self-expandable stents, balloon-expandable stents, stent-grafts, vascular grafts, cerebrospinal fluid shunts, or generally tubular implantable medical devices.

Sterilization is typically performed on medical devices, such as stents and delivery systems, to reduce the bioburden. Bioburden refers generally to the number of microorganisms with which an object is contaminated. The degree of sterilization is typically measured by a sterility assurance level (SAL) which refers to the probability of a viable microorganism being present on a product unit after sterilization. The required SAL for a product is dependent on the intended use of the product. For example, a product to be used in the body's fluid path is considered a Class III device. SAL's for various medical devices can be found in materials from the Association for the Advancement of Medical Instrumentation (AAMI) in Arlington, Va.

Radiation sterilization is well known to those of ordinary skill the art. Medical articles composed in whole or in part of polymers can be sterilized by various types of radiation, including, but not limited to, electron beam (e-beam), gamma ray, ultraviolet, infra-red, ion beam, x-ray, and laser sterilization. A sterilization dose can be determined by selecting a dose that provides a required SAL. A sample can be exposed to the required dose in one or multiple passes.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, fracture toughness, expansion ratio, coverage area, and longitudinal flexibility. Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

In some embodiments, a stent may be formed from a tube by laser cutting the pattern of struts in the tube. Such tubes are typically formed by the melt processing methods of extrusion or injection molding or by solvent processing, such as cold solvent extrusion, solvent casting, or dip coating. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

FIG. 1 depicts a tube 10 which is a cylinder with an outside diameter 15 and an inside diameter 20. FIG. 1 also depicts a surface 25 and a cylindrical axis 30 of tube 10. In some embodiments, the diameter of the polymer tube prior to fabrication of an implantable medical device may be between about 0.2 mm and about 5.0 mm, or more narrowly between about 1 mm and about 4 mm.

Figure 2:
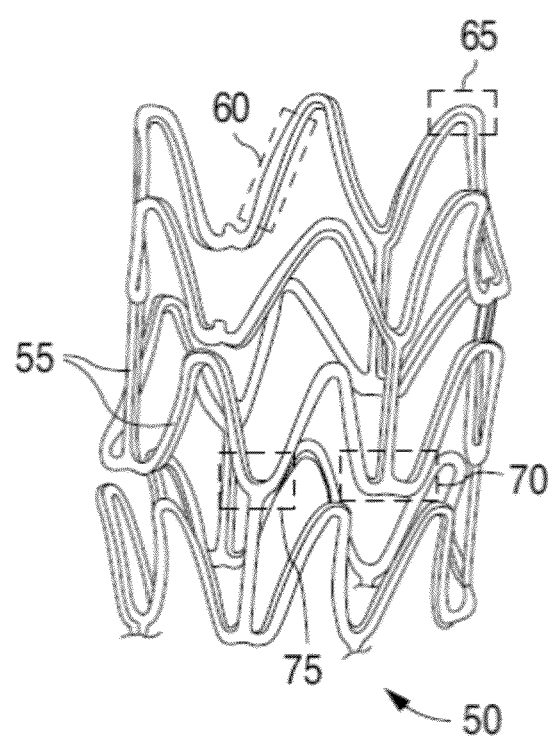
FIG. 2 depicts an example of a stent.

FIG. 2 depicts an example of a stent 50. Stent 50 includes a pattern with a plurality of interconnecting structural elements or struts 55. The embodiments disclosed herein are not limited to stents or to the stent pattern illustrated in FIG. 2. The embodiments are easily applicable to other patterns and other devices. The variations in the structure of patterns are virtually unlimited.

In general, a stent pattern is designed so that the stent can be radially compressed (crimped) and radially expanded (to allow deployment). The stresses involved during compression and expansion are generally distributed throughout various structural elements of the stent pattern. As a stent expands, various portions of the stent can deform to accomplish a radial compression or expansion.

As shown in FIG. 2, the geometry or shape of stent 50 varies throughout its structure to allow radial expansion and compression. A pattern may include portions of struts that are straight or relatively straight, an example being a portion 60. In addition, patterns may include struts that include curved or bent portions or crowns denoted as 65, 70, and 75.

The pattern that makes up the stent allows the stent to be radially compressible and expandable and longitudinally flexible. Portions such as sections 65, 70, and 75 of the stent pattern are subjected to substantial deformation as these portions bend during radial expansion and compression. Thus, these portions tend to be the most vulnerable to fracture and ultimately failure.

The cross-section of the struts in a stent may be rectangular- or circular-shaped. The cross-section of struts is not limited to these, and therefore, other cross-sectional shapes are applicable with embodiments of the present invention. Furthermore, the pattern should not be limited to what has been illustrated as other stent patterns are easily applicable with embodiments of the present invention.

The struts of the stent scaffolding can be made partially or completely from a bioresorbable, bioabsorbable, or biostable polymer. In this case, a scaffolding composed of a polymer or primarily of a polymer provides support or outward radial force to a vessel wall when implanted. A polymer for use in fabricating a stent can be biostable, bioabsorbable, bioresorbable, or bioerodable. Biostable refers to polymers that are not bioresorbable. The terms bioresorbable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

Polymers that are particularly useful for a bioresorbable or bioabsorbable stent include semi-crystalline or amorphous bioresorbable polymers, such as, bioresorbable polyesters. In particular, struts can be made mostly or completely out of bioresorbable polyesters having a glass transition temperature (Tg) above human body temperature, which is about 37° C. The reason for this is that, as indicated below, Tg, is the temperature at which the amorphous domains of a polymer change from a brittle vitreous state (also known as glassy state) to a solid deformable or ductile state. Thus, upon implantation, a stent body made of a polymer with a Tg greater than body temperature can remain rigid and resist recoil upon implantation. For example, such polymers include poly(L-lactide), and, poly(L-lactide-co-glycolide).

The tube or stent body or scaffolding of the present invention can be made in whole or in part from one or a combination of bioresorbable and bioabsorbable polymers including, but not limited to, poly(L-lactide) (PLLA), polymandelide (PM), poly(DL-lactide) (PDLLA), polyglycolide (PGA), and poly(L-lactide-co-glycolide) (PLGA). The tube or stent can be made of a random, alternating, or block copolymer of the above polymers and one or more of the following: polycaprolactone (PCL), poly(trimethylene carbonate) (PTMC), polydioxanone (PDO), poly(4-hydroxy butyrate) (PHB), and poly (butylene succinate) (PBS). The PLGA used can include any molar ratio of L-lactide (LLA) to glycolide (GA). In particular, the stent can be made from PLGA with a molar percentage of (LA:GA) including 85:15 (or a range of 82:18 to 88:12), 95:5 (or a range of 93:7 to 97:3), or commercially available PLGA products identified as having these molar ratios. The glass transition temperatures of several polymers are shown in Table 1.

TABLE 1

Glass transition temperatures of polymers.

| Polymer | Glass-Transition Temp (° C.)[1] |
|---------|-------------------------------|
| PGA     | 35-40                         |
| PLLA    | 60-65                         |

TABLE 1-continued

Glass transition temperatures of polymers.

| Polymer | Glass-Transition Temp (° C.)[1] |
|---|---|
| PDLLA | 55-60 |
| 85/15 PLGA | 50-55 |
| 75/25 PLGA | 50-55 |
| 65/35 PLGA | 45-50 |
| 50/50 PLGA | 45-50 |

[1]Medical Plastics and Biomaterials Magazine, March 1998.

An exemplary embodiment is a PLLA scaffolding with a coating including PDLLA and everolimus. The thickness of the struts can be between 140-160 microns and the thickness of the coating can be 2 to 3.5 microns.

The radial strength of a stent and the fracture toughness of polymeric stent material are important properties for proper functioning of a stent. As indicated above, a stent is deployed by expanding it to an increased diameter at an implant site in a vessel which can be greater than the as-cut diameter of the stent. The deployed stent must have sufficient radial strength to apply an outward radial force to support the vessel at an increased diameter for a period of time. The crown regions of the deployed stent are under high stress and strain during expansion and after deployment, and thus susceptible to fracture. Polymers tend to have lower strength to weight ratio than metals. Therefore, it is important to increase the strength of the structural elements so that the stent has sufficient radial strength.

The fabrication process of a polymer stent can include processing steps that increase the radial strength as well as the fracture toughness of the polymeric structural elements. In particular, the manufacturing process further includes radially expanding the tube to an expanded diameter and cutting a stent pattern in the expanded tube. The tube is radially expanded to increase its radial strength, which can also increase the radial strength of the stent. The radial expansion process tends to preferentially align the polymer chains along the radial or hoop direction which results in enhanced radial strength. The radial expansion step is crucial to making a stent scaffolding with thin struts (e.g., 140-160 microns thick) sufficiently strong to render and keep a lumen patent after implantation. The tube can also be axially elongated or extended as well during the expansion process to provide biaxial orientation.

Fracture toughness is enhanced for a semi-crystalline polymer by minimizing the size of crystalline domains, aligning the molecular chain orientation, and achieving a desirable or an optimal amorphous/crystalline ratio. The crystallinity provides strength and stiffness (high modulus) to the polymer which is needed for supporting a vessel. However, if the degree of crystallinity is too high, the polymer may be too brittle and is more susceptible to fracture. The degree of crystallinity for a PLLA scaffolding should be 10-40%, or more narrowly, 30-40%.

Since crystals nucleate and grow between Tg and the melting temperature of a semi-crystalline polymer, the size of crystalline domains and degree of crystallinity depend on process parameters of the radial expansion process, such as the expansion temperature, heating rate, and time spent above Tg. Generally, smaller crystals are favored or generated at lower temperatures closer to Tg than the melting temperature. For example, for a PLLA tube, an expansion temperature of 65-120° C. is preferred.

The tube is radially expanded by heating the tube to a temperature above Tg and, in the case of a semi-crystalline polymer, below the melting point of the polymer. Upon expansion the tube is cooled to below the Tg of the polymer, typically to ambient temperature, to maintain the tube at an expanded diameter.

A stent pattern is cut into the expanded tube, for example, by laser machining. After cutting a stent pattern into the expanded tube, the stent scaffolding may then be optionally coated with a drug delivery coating which can include a polymer and a drug. In order to make the stent ready for delivery, the stent is secured to a delivery balloon. In this process, the stent is compressed to a reduced diameter or crimped over the balloon. During crimping and in the crimped state, the crowns of the stent are subjected to high, localized stress and strain. In particular, the inside or concave region of the crowns is subjected to high compressive stress and strain. Thus, the stent during crimping and in the crimped state is susceptible to cracking. It is important to minimize cracking in this state, since this can have a negative impact on the ability of the stent to support a vessel upon deployment.

After the stent is mounted on a catheter the catheter and stent are placed into a package for storage until implantation. Stents and stent delivery assemblies are typically stored, transported, as well as sterilized in sealed storage containers. Such containers are adapted to protect the assembly from damage and environmental exposure (humidity, oxygen, light, etc.) which can have an adverse effect on the stent. Storage containers for a stent and delivery system can be designed to be any convenient form or shape that permits the effective enclosure of a stent and delivery system assembly contained therein. The container, however, may be compact and shaped so as to minimize storage space occupied by the container. A container intended primarily to protect the stent and delivery system from environmental exposure can be a pouch or sleeve.

Following fabrication and packaging of a device, the device typically is stored for an indefinite period of time prior to use in a patient. The storage period can be days, weeks, or months and is typically not the same for every individual device.

The stent and catheter may then be sterilized by exposure to radiation. Radiation exposure can degrade the properties of the polymers and drugs. In particular, the radiation can generate active species and induce chemical reactions in the polymer and drug. High-energy radiation such as e-beam and gamma radiation tends to produce ionization and excitation in polymer molecules. These energy-rich species undergo dissociation, subtraction, and addition reactions that degrade the properties of a polymer in a sequence leading to chemical stability. The stabilization process can occur during, immediately after, or even days, weeks, or months after irradiation which often results in physical and chemical cross-linking or chain scission. Chain scission can result in a reduction in molecular weight which can adversely affect mechanical properties and degradation properties, in the case of a degradable polymer. Resultant physical changes can include embrittlement, discoloration, odor generation, stiffening, and softening, among others.

Exposing a polymer to e-beam radiation causes the generation of free radicals in the polymer. The degradation of polymer properties has been associated with free radical generation caused by the radiation exposure. Free radicals generated can be come trapped with the polymer. The degradation of the polymer properties may continue as the trapped free radicals continue to decay after the initial radiation exposure. "Free radicals" refer to atomic or molecular species with unpaired electrons on an otherwise open shell configuration. Free radicals can be formed by oxidation reactions. These unpaired electrons are usually highly reactive, so radicals are likely to take part in chemical reactions, including chain reactions. The free radicals formed due to radiation exposure can react with the polymer chains to cause chain scission. These reactions are dependent on e-beam dose, dose rate, the e-beam environment (type of gas), humidity, and temperature.

The molecular weight of PLLA has been observed to decrease after sterilization with e-beam radiation. Additionally, the presence of free radicals in the sterilized PLLA has been monitored and the concentration of the free radicals is seen to decrease with time after e-beam exposure. The decrease in concentration is believed to be primarily due to the termination of the free radicals through reactions with the polymer chain which results in chain scission. The concentration of free radicals does not decay to zero until about 2 months under inert gas packaging condition and it is believed that molecular weight degradation occurs throughout this time period.

Therefore, a method is needed which accelerates the reduction in free radical concentration after sterilization in a manner that reduces or eliminates chain scission of the polymer. For example, a method is needed to promote free radical combination and termination rather than free radical termination through chain scission.

The various embodiments of the present invention include exposing a stent made from or including a polymer to a temperature above ambient after sterilization with radiation. The exposure to the increased temperature increases the temperature of the stent and reduces the chemical degradation of the polymer due to the sterilization. Therefore, the exposure to increased temperature chemically stabilizes the polymer of the stent. The chemical degradation includes reduction in molecular weight of the polymer that may be due to chain scission arising from the radiation exposure. The increase in temperature after e-beam exposure reduces the concentration of free radicals and accelerates the free radical decay kinetics. As discussed and shown below, exposing a PLLA stent to a temperature above ambient dramatically accelerates the reduction in concentration of the free radicals after radiation exposure.

In some embodiments after e-beam sterilization, the stent is heated by exposing the stent to an environment at a specified temperature above ambient temperature. For example, the stent can be exposed to a temperature controlled oven in which the temperature can be precisely controlled at a specified temperature or within a temperature range.

The sterilization may include exposing the stent to e-beam radiation or some other type of radiation. The radiation exposure can be performed with a conventional e-beam radiation source. In some embodiments, the stent may be exposed to a dose between 10-40, 20-35, or 20-30 kGy. In other embodiments, the stent may be exposed to a dose between 20-31 kGy or, more narrowly, 20-27.5 kGy.

As discussed above, below Tg, polymer chains have very low mobility. Without being limited by theory, it is believed that when free radicals that are generated in a polymer that is well below its Tg, the free radicals are trapped by polymer chains that have very low mobility, for example, those chains near or at the amorphous-crystalline interface. However, it is believed that free radicals can be trapped even in completely amorphous polymers with no crystallinity. The trapping of free radicals is typical for a polymer such as PLLA with a Tg above body temperature that is sterilized at or near ambient temperature. Since the free radicals generated have very low mobility, the probability of free radicals combining and terminating is relatively low due to their low mobility. The probability of such self-terminating reactions are much lower than chain scission reactions with polymer chains that trap the free radicals. As the temperature of the polymer increases closer to or above Tg, polymer chain mobility increases. The mobility of free radicals increases which increases the probability of self-terminating reactions.

The stent heating due to the exposure to increased temperature should be performed at temperatures and duration that inhibit loss of properties generated by the radial expansion and in later pressing steps. These properties include enhancements in radial strength and toughness due to alignment of polymer chains, the small crystalline domains, and the degree of crystallinity. Exposure of the stent made from a polymer to temperatures above the Tg of the polymer, particularly for prolonged periods, can modify these properties. Such exposure could negatively impact the performance of the stent when implanted. Heating the stent polymer at a temperature above Tg can result in changes in the crystallinity, crystal size, and alignment of polymer chains.

Thus, in some embodiments, the exposure temperature, and thus the stent temperature, can be maintained at a temperature below the Tg of the polymer in the stent. In particular, the temperature can be maintained at a temperature below the Tg of the polymer of the support structure, such as a scaffolding, to avoid modifying chain orientation, degree of crystallinity, and crystal size. In the case of a block copolymer that includes polymer blocks with a Tg above body temperature, the exposure temperature may be maintained below the Tg of such blocks.

In some embodiments, the stent is exposed to a specified temperature or temperature range which is maintained for a duration of time, followed by reducing the temperature of exposure, for example, back to ambient temperature.

In certain embodiments, the specified exposure temperature for an arbitrary polymer with a Tg above body temperature (up to the Tg of the polymer) can be, in degrees Celsius, 25-30, 30-35, 35-40, 40-45, 45-50, 50-55, 55-60, 60-65, 65-70, 70-75, 75-80, 80-85, 85-90, 90-95, 95-100, or greater than 100. The specified exposure temperature can be in ranges of 1 or 2 degrees Celsius increments from 25° C. to the Tg of the polymer. The temperatures above and disclosed elsewhere herein can also apply to the actual temperature of the stent.

The specified exposure temperature for PLLA in degrees Celsius, can be, 25-30, 30-35, 35-40, 40-45, 45-50, 50-55, 55-60. The specified exposure temperature for PLLA in degrees Celsius can also be 44-46, 46-48, 48-50, 50-52, 52-54, 54-56, 56-58, 58-60° C. The specified exposure temperature can be any temperature, in degrees Celsius, between 25-60, 60-62, and 62-64° C.

The specified exposure temperature for 85/15 and 75/25 PLGA can be, 25-30, 30-35, 35-40, 40-45, and 45-50. The specified exposure temperature for 85/15 and 75/25 PLGA can also be, 34-36, 36-38, 38-40, 40-42, 42-44, 44-46, 46-48, 48-50° C. The specified exposure temperature can be any temperature between 25-50, 50-52, 52-54° C.

The duration of exposure at the specified temperature in combination with any of the disclosed temperature embodiments can be 0.5 to 10 hours, less than 0.5 hour, or greater than 10 hours. The duration of exposure, in combination with any of the disclosed temperature embodiments can be 0.5-1, 1-1.5, 1.5-2, 2-2.5, 2.5-3, 3-3.5, 3.5-4, 4-4.5, 4.5-5, 5-5.5, 5.5-6, 6-6.5, 6.5-7, 7-7.5, 7.5-8, 8-8.5, 8.5-9, 9-9.5, 9.5-10 hours.

In further embodiments, stabilizing a polymer in a stent can be performed by cycling the exposure temperature, and, thus the actual temperature of the stent. The temperature cycling can be performed by increasing the exposure temperature, decreasing the exposure temperature, and then repeating the increasing and decreasing one or more times. In such embodiments, the exposure temperature may be increased to a peak temperature followed by a decrease to a minimum temperature. The peak temperature and minimum temperature can be the same every cycle or can be vary from cycle to cycle.

The temperature cycling exposure to the stent can be performed, for example, by disposing the stent in a temperature-controlled oven. The oven can be programmed to expose the stent to a selected time versus temperature profile.

In some embodiments, the exposure temperature is decreased immediately upon reaching the peak temperature. In some embodiments, the exposure temperature increases immediately upon reaching the minimum temperature. In other embodiments, the temperature profile can have a dwell period at the peak temperature, minimum temperature, or both. In the embodiments with a dwell period, the exposure temperature is maintained at the peak temperature for a dwell time period prior to decreasing the temperature. Also, the minimum temperature is maintained for a dwell time period prior to increasing the temperature.

In the temperature cycling embodiments, the peak exposure temperature can include the above disclosed temperatures or ranges. The peak exposure temperatures may also be greater than the Tg of the stent polymer. For example, the peak exposure temperature for PLLA may be 65-70, 70-75, 80-85, or more than 85° C. However, the duration of time above Tg should be adjusted so that the properties of the stent polymer are not adversely affected as discussed above.

The minimum temperature can be ambient temperature or greater than ambient A temperature greater than ambient can be 25-30, 30-35, or 35-40° C.

In exemplary embodiments, the stent can be subjected to two, three, four, or more than four cycles. The stent can be exposed to temperature cycles between sub-ambient and a peak temperature less the Tg of the polymer. In the case of a PLLA stent, the cycling can be between a temperature in the ambient temperature or greater than ambient ranges disclosed above and any temperature or temperature range between 35-60° C. In some embodiments, all temperatures the cycling are above ambient and below Tg.

In some embodiments, the duration of a cycle can be measured from a time of a minimum to maximum and return to minimum temperature. The duration of a cycle can be 1-10 min. More narrowly, the duration of a cycle can be 1-2, 2-3, 3-4, 4-5, 5-6, 6-7, 7-8, 8-9, 9-10, 2-4, 2-5, 2-6, 3-5, 3-6, or 5-10 min. In some embodiments, the frequency of the temperature cycles can be 5-30, 5-20, 5-10, 10-20, 12-20, or 15-20 cycles per hour.

It is believed that temperature cycling tends to further accelerate the stabilization of the polymer, in particular, accelerate the reduction in free radicals. Therefore, stabilizing with temperature cycling may reduce the free radical concentration to zero or close to zero in total exposure time that is shorter than a continuous exposure at a specified temperature.

Definitions

Ambient temperature can correspond to any temperature between 20 and 30° C.

All ranges disclosed include endpoints of the ranges.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus is the initial slope of a stress-strain curve, and therefore, determined by the linear hookean region of the curve. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below their Tg, many polymers tend to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

Elongation to Break is the strain on a sample when it breaks. It is usually is expressed as a percent.

"Toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle substances are strong, but cannot deform very much before breaking.

EXAMPLE

The following example illustrates the effect on free radical concentration of exposing stent made from a polymer to a temperature above ambient temperature after sterilization with radiation. The stents used in the study are a scaffolding made from PLLA.

Figure 3:
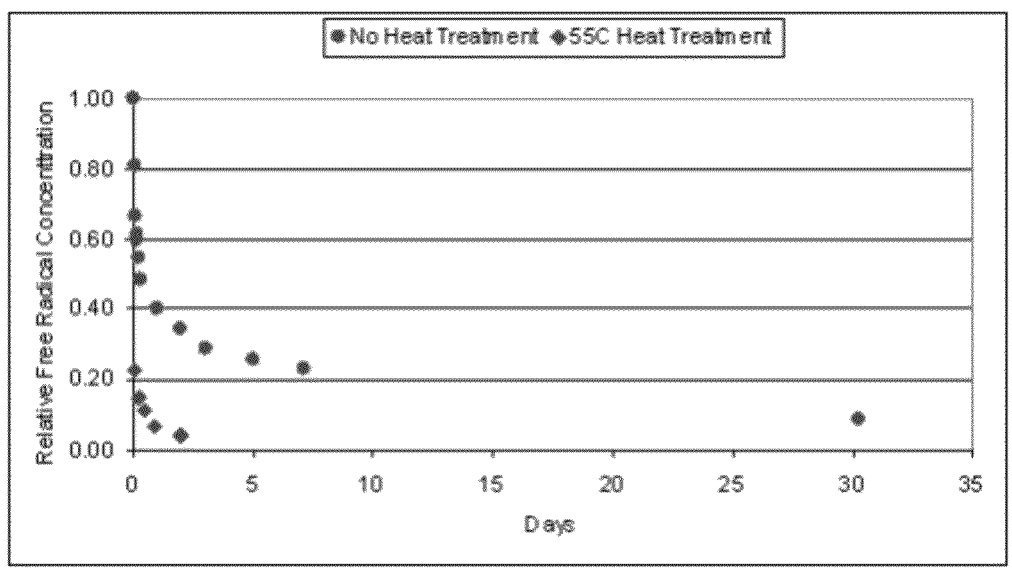
FIG. 3 depicts the relative free radical concentration of a polymeric stent with heat treatment and the stent with no heat treatment.

FIG. 3 and Table 2 depict the relative free radical concentration of the stent with heat treatment and the stent with no heat treatment as a function of time after e-beam sterilization. The relative free radical concentration is the free radical concentration normalized to the initial concentration immediately after e-beam sterilization. The stents in the study were sterilized by e-beam radiation with a dose of 31 kGy. The stents were packaged in a foil pouch (MarvelSeal 360—Nylon/Aluminum/LDPE) made by Oliver-Tolas of Grand Rapids, Mich. The packages were sealed with an argon atmosphere inside.

TABLE 2

Relative Free Radical Concentration of stents without and with heat treatment after e-beam sterilization.

| No Heat Treatment | | | 55° C. Heat Treatment | | |
| --- | --- | --- | --- | --- | --- |
| Days | Hours | Free Radical Concentration | Days | Hours | Free Radical Concentration |
| 0 | 0 | 1.00 | 0 | 0 | 1.00 |
| 0.04 | 1 | 0.81 | 0.08 | 2 | 0.23 |
| 0.08 | 2 | 0.66 | 0.21 | 5 | 0.15 |
| 0.13 | 3 | 0.61 | 0.42 | 10 | 0.11 |
| 0.17 | 4 | 0.60 | 0.92 | 22 | 0.07 |
| 0.25 | 6 | 0.54 | 2.00 | 48 | 0.04 |
| 0.33 | 8 | 0.48 | | | |
| 1.00 | 24 | 0.40 | | | |
| 2.00 | 48 | 0.35 | | | |
| 3.00 | 72 | 0.29 | | | |
| 5.00 | 120 | 0.26 | | | |
| 7.13 | 171 | 0.23 | | | |
| 30.21 | 725 | 0.09 | | | |

Each data point for both no heat treatment and heat treatment after e-beam exposure was generated by an individual packaged stent sample. The data for heat treatment was generated from stents subjected to a heat treatment in an oven for 2, 5, 10, 22, and 48 hours at 55° C. The free radical concentration for the stent samples not subjected to a heat treatment and the stent samples subjected to heat treatment was measured using Electron Spin Resonance (ESR), also known as Electron Paramagnetic Resonance (EPR) in Abbott Vascular, Temecula, Calif.

As shown by FIG. 3, the free radical concentration decays much faster with heat treatment than without. The free radical concentration is still at about 0.09 at 35 days with no heat treatment while the free radical concentration is less than half of that, 0.04, after only about 2 days.

Figure 4:
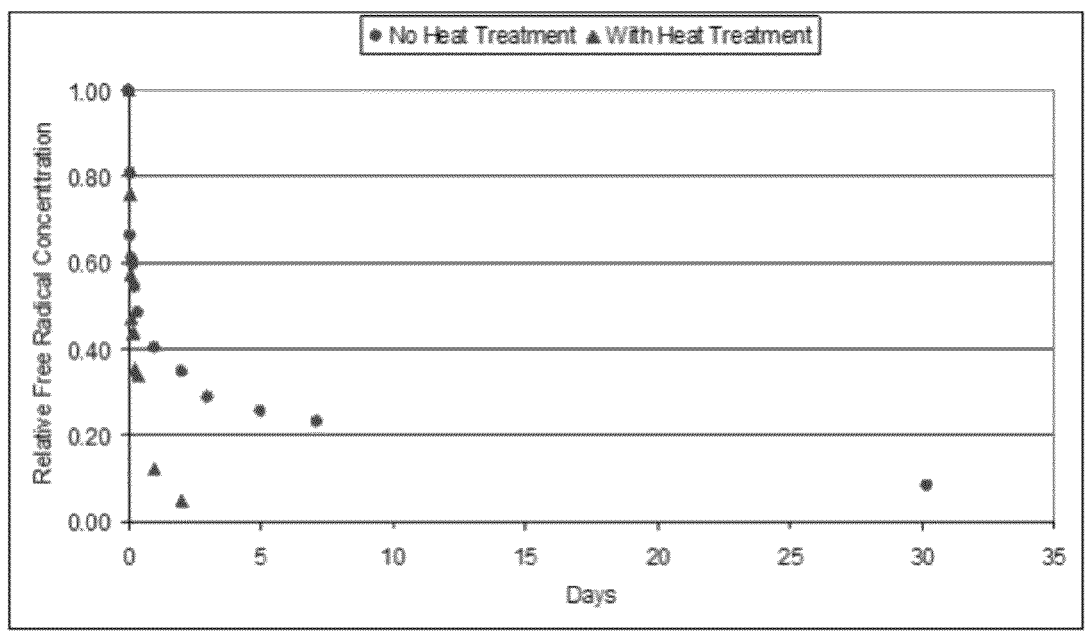
FIG. 4 depicts the relative free radical concentration of a polymeric stent with heat treatment and the stent with no heat treatment.

FIG. 4 also depicts the relative free radical concentration of the stent with heat treatment and the stent with no heat treatment. The data for the no heat treatment is the same as that in FIG. 3. One data point in FIG. 4 for heat treatment was generated from a stent subjected to a heat treatment in a oven for 5 hours at 55° C., which is from FIG. 3. The additional data points for the curve with heat treatment are predicted by pseudo first order decay kinetics with free radical concentration of sample after 5 hours at 55° C. heat treatment. A comparison of FIG. 3 and FIG. 4 shows that the kinetic model predicts a greater relative free radial concentration with time than the experimental data. Therefore, the model may be used to select a desirable heat treatment temperature. For example, the relative free radical concentration can be measured for various temperatures and the decay profile may then be calculated from the single data points. The decay profiles may be expected to provide an upper bound to the decay of the free radial concentration vs. time for the various temperatures.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of stabilizing a stent comprising:
    sterilizing a stent made of polymer with radiation exposure, wherein the radiation exposure generates free radicals within the polymer, wherein the polymer is poly(L-lactide);
    exposing the stent to a temperature to increase a temperature of the stent for a duration of time, wherein the increase in temperature reduces the concentration of free radicals and increases the decay kinetics of free radicals leading to their disappearance and thereby reducing the chemical degradation of the polymer due to the sterilization,
    wherein the exposure is performed at the temperature that avoids modifying degree of crystallinity, crystal size, and polymer chain alignment of the polymer of the stent, and wherein the temperature of exposure is in a temperature range consisting of above ambient temperature to less than the glass transition temperature (Tg) of the polymer.

2. The method of claim 1, wherein the exposure to the increased temperature is maintained for 1 to 6 hours.

3. The method of claim 1, wherein the radiation is e-beam radiation.

4. The method of claim 1, wherein the radiation exposure is between 20 and 31 kGy.

5. The method of claim 1, wherein the stent is contained within a sealed pouch.

6. The method of claim 1, wherein the temperature of exposure is between 50 to 55° C.

* * * * *